(12) United States Patent
Shnier

(10) Patent No.: US 6,590,661 B1
(45) Date of Patent: Jul. 8, 2003

(54) OPTICAL METHODS FOR SELECTIVELY SENSING REMOTE VOCAL SOUND WAVES

(76) Inventor: J. Mitchell Shnier, 25 Lower Links Road, Toronto, Ontario (CA), M2P 1H5

(*) Notice: Subject to any disclaimer, the term of this patent is extended or adjusted under 35 U.S.C. 154(b) by 0 days.

(21) Appl. No.: 09/487,297

(22) Filed: Jan. 19, 2000

Related U.S. Application Data

(60) Provisional application No. 60/116,632, filed on Jan. 20, 1999.

(51) Int. Cl.[7] .................................. G01N 21/00
(52) U.S. Cl. .................................. 356/432; 356/437
(58) Field of Search ..................... 356/432, 437; 73/646, 861.18; 435/808; 381/172; 250/227.23, 227.18, 205; 359/172

(56) References Cited

U.S. PATENT DOCUMENTS

| | | |
|---|---|---|
| 3,622,791 A | 11/1971 | Bernard |
| 3,633,705 A | 1/1972 | Teder |
| 3,895,188 A | 7/1975 | Ingraham |
| 4,071,753 A | 1/1978 | Fulenwider |
| 4,166,932 A | 9/1979 | Selway |
| 4,479,265 A | 10/1984 | Muscatell |
| 4,566,135 A | 1/1986 | Schmidt |
| 4,979,820 A | 12/1990 | Shakkottai et al. |
| 5,024,526 A * | 6/1991 | von Redwitz ............... 356/339 |
| 5,029,023 A | 7/1991 | Bearden et al. |
| 5,146,083 A | 9/1992 | Zuckerwar et al. |
| 5,200,610 A | 4/1993 | Zuckerwar et al. |
| 5,202,939 A | 4/1993 | Belleville et al. |
| 5,247,490 A | 9/1993 | Goepel et al. |
| 5,262,884 A | 11/1993 | Bucholz |
| 5,392,117 A | 2/1995 | Belleville |
| 5,804,702 A * | 9/1998 | Hovde et al. ............... 73/24.04 |
| 6,014,239 A * | 1/2000 | Veligdan ..................... 359/149 |
| 6,034,760 A * | 3/2000 | Rees .......................... 356/28.5 |
| 6,072,882 A * | 6/2000 | White et al. ............... 381/94.1 |
| 6,369,387 B1 * | 4/2002 | Eckles ........................ 250/343 |

OTHER PUBLICATIONS

Snell, F.K. and Ettre, L.S., editors, Encyclopedia of Industrial Chemical Analysis, 1969 Edition, p. 264, vol. 8, Published by John Wiley & Sons, Inc, New York.

* cited by examiner

Primary Examiner—Zandra V. Smith
Assistant Examiner—Gordon J Stock

(57) ABSTRACT

Methods for remotely sensing sound waves in an optically transparent or semitransparent medium through detecting changes in the optical properties of the medium, which are caused by the sound waves. For example, to implement a microphone that can sense sound at a distance from the sound source. The variations in the attenuation or the phase of a beam of light that is received after passing through the sound waves are sensed and converted to an electrical or other signal. For the attenuation method, the wavelength of the beam of light sensed is selected to be one that is highly attenuated by a constituent of the medium, so that the changing instantaneous pressure of the medium due to the sound pressure waves can be detected through the changing light attenuation due to the changing density of the air along the light path. For the phase shift method, the velocity of light, and therefore its phase is changed by the changing density of the air due to the sound waves, and this can be detected through interferometric means.

6 Claims, 11 Drawing Sheets

OPTICAL METHODS FOR SELECTIVELY SENSING REMOTE VOCAL SOUND WAVES

This application claims benefit of Provisional application Serial No. 60/116632 filed Jan. 20, 1999

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

This invention relates to methods for sensing sound waves, and in particular, using optical means to detect sound waves through certain corresponding changes in the optical properties of air or other optically transparent or semitransparent medium through which the sound propagates.

Current methods for sensing sound waves typically involves the sound waves impinging on a diaphragm or other mechanical surface, and then using an electrical, or in some cases optical, means to detect the movement of said diaphragm or other mechanical surface. Such traditional microphones typically need to be located close to the source of the sound waves so that the diaphragm moves according to the sound waves to be sensed with adequate fidelity and signal strength, and so that the effects of noise and other undesired sounds is minimized. Locating the microphone close to the source of the sound can be problematic, for example, when the microphone is being used to monitor sound waves from a person who needs to be somewhat mobile (for example, a performer on a stage) or does not have a hand free to hold the microphone. Also, traditional microphones typically obstruct the view of a performer's face. And often microphones need to be hidden from view, for example for motion picture actors and people on television. Or surveillance and security applications may require that the microphone be located a distance from the sound source. Failings with traditional microphones themselves are that they: require cables or other transmission means to relay their sensed sounds to a receiving device, require careful mechanical design and assembly to provide good performance, due to their mechanical nature they have a limited range of frequencies to which they are sensitive, and are often fragile. Also, due to environmental factors, such as electromagnetic fields, pressure, and temperature, or the presence of corrosive or combustible gases, it may be difficult to get acceptable performance from such traditional microphones. And the connectors and cables of traditional microphones are also expensive, subject to wear and damage, and are a source of electromagnetic field induced and electromechanical contact noise. Finally, high quality microphones are large, and as is often seen at press conferences, mounting larger numbers of them on a podium can be a problem.

Prior art has attempted to solve these limitations in a variety of ways.

Wireless microphones are widely used by business meeting presenters, stage performers and other actors. Typically a small battery-operated radio-frequency, infrared light or ultrasonic sound transmitter unit (about the size of a pager) is clipped to the presenter's belt, and a cable leads from this transmitter to a small microphone, which is often then clipped to the presenter's clothing, as close to their mouth as is convenient. The transmitter transmits the presenter's audio to a receiving unit typically located within 2 to 30 meters, and this receiving unit is then connected to an audio amplifier, a recording device or other equipment. There are many shortcomings of this method. For example, the transmitter's battery can fail at an inopportune time. Radio frequency or other types of interference from other equipment or transmitters can disrupt or degrade the signal. The requirements of routing the microphone cable through one's clothing, finding a place to mount the transmitter, and mounting the microphone close to the presenter's mouth are often a problem requiring undesirable trade-offs of audio quality versus convenience. For higher audio quality, larger microphones must be used and positioned in front of the performer's mouth (as is often seen by singers at concerts), and these obstruct the audience's view of the performer's face. Also, each presenter must have a transmitter; and this can be costly, and requires coordination of the radio frequencies used. Alternatively, sharing a unit is difficult as it is awkward to quickly transfer it to another person. Finally, the whole system of microphone, battery, transmitter and receiver is time-consuming to set-up, trouble-shoot and transport.

High-quality microphones are often mounted on long poles. Such boom microphones are often used for television programs and motion pictures. These can be mounted on wheeled dollies; in which case they are they are large, and have heavy counterweights so that the booms can be up to 5 to 10 meters in length. Or the boom microphones can be hand-held, in which case the boom length is typically quite limited, for example to 2 or 3 meters. In any case, such boom microphones typically require a full-time operator to ensure that the microphone itself is as close to the (moving) performer as possible, while staying out of the field of view of the camera (which can often change to a wider view, requiring the microphone to first be moved). Also, the maximum distance from the actor to the microphone is limited by the audio quality required (background noise and reduced frequency response are a problem at more than a meter or two).

U.S. Pat. No. 3,633,705 to Teder describes a microphone with a tubular housing to aid in rejecting unwanted noise. Such microphones are large, and still need to be close to the sound source, are effective for only some frequencies and directions of noise and require careful mechanical assembly.

A microphone mounted near the focus of a paraboloid-shaped plastic reflector is often used to increase the directionality of a microphone, so that such microphones can be located a distance from the sound source, as in U.S. Pat. No 3,895,188 to Ingraham. Due to the nature of such reflected sound waves, such systems have a poor frequency response characteristic, are often too sensitive to wind, handling and other noise sources, pick-up undesired sounds behind the intended sound source, and require trial-and-error focussing adjustments according to the distance to the sound source.

Sensing sound waves and other vibrations (such as those from rotating machinery) through optical means is the subject of much prior art. A method of sensing vibrations and other very small movements of surfaces is described in U.S. Pat. No. 5,029,023 to Bearden et al. This involves coherent laser lit reflected from the measured surface to be fed back into the laser cavity and measuring the resulting varying light output of the laser. The distance over which such a system operates is limited by the coherence length of the laser light source, which is typically less than a meter. Also, to sense sound would require a reflective diaphragm to be located near the sound source, and for this diaphragm to be precisely aimed to return the laser light. Also, the physical characteristics of the diaphragm affect the fidelity of the sensing of the sound waves. Such complex and high-cost systems are typically more suited to experimental and laboratory use than industrial and commercial applications. U.S. Pat. Nos. 5,202,939 and 5,392,117 to Belleville et al. describe an interferometry-based method for detecting small displacements, such as due to the stress of a structural member which is located at the end of an optical fiber cable. Such systems are suited more to instrumentation applications, and require a fiber optic cable to be run all the way to the sound source.

U.S. Pat. Nos. 5,146,083 and 5,200,610 to Zuckerwar et al., and U.S. Pat. No. 5,262,884 to Buchholz describe systems which use a fiber optic cable to illuminate an optical element, with said optical element being mounted on a flexible membrane or diaphragm which vibrates according to the ambient sound waves. The motion of the optical element relative to the illuminating fiber optic cable affects the amount of light directed back to the same or a second fiber optic cable, and this is sensed at the far end of the fiber optic cable. U.S. Pat. Nos. 3,622,791 to Bernard and U.S. Pat No. 5,247,490 to Goepel use a mirror mounted on a diaphragm, which is located so that it moves according to the ambient sound waves, and the motion of the mirror is detected through interferometry. U.S. Pat. No. 4,479,265 to Muscatell describes a cylindrical microphone with a variety of reflecting surfaces which move according to the ambient sound, and this movement is detected by tracking the Doppler shift, beat frequency with a reference beam, or movement of interference fringes, of laser light reflected from these surfaces. Pat. Nos. 4,071,753 to Fulenwider et al. and U.S. Pat. No. 4,166,932 to Selway describe a microphone in which the alignment of two optical fibers is affected by sound waves impinging on a diaphragm, so that the amount of light transmitted through the optical fibers varies according to the sound waves. U.S. Pat. No. 4,566,135 to Schmidt describes a microphone where a membrane in close proximity to the surface of a transparent material is affected by sound waves, so that the reflection of light from a light source in the transparent material, to the surface below the membrane, and to a light sensor within the transparent material is affected, so that the intensity of the received light varies according to the sound waves. All of these methods require a membrane, diaphragm or other surface which must be close enough to the sound source that it vibrates according to the sound. This results in many of the same problems as locating a traditional microphone.

U.S. Pat. No. 4,979,820 to Shakkottai et al. describes a laser light and interferometry-based method of remotely detecting sound waves due to leaks. This method requires a special retroreflective target with a printed Ronchi grating to be located on the opposite side of the sound source. It also requires precise alignment of the split beams of laser light, and a micrometer adjustment to match the pitch of the interference lines to the Ronchi grating.

Clearly, there is a need for a method of sensing sound waves that overcomes these shortcomings.

BRIEF SUMMARY OF THE INVENTION

The present invention describes several optical methods for sensing sound waves, as these have substantial advantages over the prior art, for many applications.

It is an object of the invention to sense sound waves at a distance from the sound source, and that no equipment, device, surface, diaphragm or membrane need be located at or near the sound source, and only a simple reflecting surface or light source need be located past the sound source.

It is a further object of the invention that it provide great selectivity of the sound source sensed, both in the direction of the sound source relative to the invention, and in the direction of propagation of the sound waves.

It is a final object of the invention to sense sound without dependence on the; careful mechanical design, frequency response, temperature or other environmental or handling requirements or characteristics of a diaphragm, membrane or other sound wave responsive surface.

The present invention overcomes important limitations and requirements of traditional microphones.

In one embodiment the present invention, light with a wide range of wavelengths—for example, ambient light or a beam of light generated for this purpose—illuminates means for detecting the optical characteristics of the light after it has passed through the sound waves to be sensed, such means for detecting the optical characteristics of the light being referred to as an "optical receiver" herein. Through the use of a diffraction grating, interference filter or other means, the optical receiver in this embodiment is designed to be sensitive only to specific wavelengths of light, those being the wavelengths which are highly absorbed by a specific constituent of air.

In another embodiment of the present invention, the light source emits specific wavelengths, those being the wavelengths absorbed by a specific constituent of air. This embodiment eliminates or simplifies the requirement for optical filtering within the optical receiver.

In another embodiment of the present invention, more than one optical receiver is used to; track variations in the output of the light source to reduce the noise which would be caused by such variations, determine the direction of propagation of the sound waves, provide increased or decreased sensitivity to particular wavelengths of sound, or other purpose.

In another embodiment of the present invention, the narrow band light source emits coherent light, and this light is split into a first and second beam. The first beam is reflected back to the optical receiver, and the second beam passes through the sound waves, after which it is recombined with the first beam within the optical receiver.

In all cases, a path of light between the light source and the optical receiver passes through the sound waves to be detected.

Sound waves are alternately compressed and rarefied air (or whatever medium through which the sound waves are propagating). That is, they are propagating waves of air which are at periodically slightly more, and later slightly less, pressure (and density) than typical atmospheric air. The longer-term atmospheric air pressure depends on the altitude, weather conditions and other factors, but is typically 97,000 to 106,000 $N/m^2$ (the units are newtons per square meter, and these are also referred to as Pascals, which are abbreviated as Pa) near sea level. In air, sound waves propagate somewhat spherically from the sound source at the speed of sound, which is approximately 344 m/s at 21° C. and typical atmospheric pressures. That is, sound waves continuously change air's density. For example, a 1,000 Hz pure tone will sinusoidally increase and decrease the density or the air 1,000 times per second. Similarly, the density of each of the constituents of the air (such as nitrogen, oxygen, carbon dioxide and water vapor) will also sinusoidally increase and decrease 1,000 times per second.

The constituents of air, for example, each have a distinctive spectrum of wavelengths of light which the constituents absorb, due to the resonance and other characteristics of the constituent's molecular bonds, and other factors. For example, carbon dioxide gas highly absorbs (and therefore attenuates) light at wavelengths of 2.69 $\mu$m, 2.76 $\mu$m and 4.25 $\mu$m, and water vapor absorbs light at wavelengths of 2.66 $\mu$m and 2.73 $\mu$m. Identifying and quantifying substances through measuring these absorptions is the basis for the field of atomic absorption spectrophotometry, which is also referred to as optical spectroscopy. The amount of attenuation (this is called the absorbance) of a band of wavelengths of light due to absorption by a particular constituent of air is proportional to the density of that constituent. Since sound waves affect the density of air (and therefore of its constituents), by detecting the resulting changing attenuation of light, sound waves passing through the path of the light can be detected.

There is relatively little change in the density of the air, as averaged along a path in the direction of propagation of a sound wave (that is, longitudinally), since the total number of air molecules along the path remains mostly constant (except for the small amount of movement past the ends of the path). However, for a light path that is transverse to (that is, across) the direction of propagation of the sound waves and which passes near the sound source, the increase and decrease in the density of air due to the sound waves can be calculated, and shown to be a measurable amount.

Further, to better detect sounds from a person or animal at a distance, the changing intensity of a wavelength of light which is highly absorbed by carbon dioxide or water vapor could be monitored, since these constituents of air have much higher concentrations in exhaled air and therefore near the mouth of people and animals, and much lower concentration (and therefore attenuation) elsewhere along the light path.

The optical receiver may employ a photodetector to directly measure the changes in the intensity of the received light, or another method of measuring the changing optical characteristics of the light beam passing through the sound waves, such as measuring the changing density of a selected constituent of the air by modulating the light beam and measuring the resulting heating of the constituent through acoustic monitoring.

Alternatively, the greater the density of air (for example, due to sound waves), the slower the velocity of propagation of light. Therefore, a light beam which passes transversely through sound waves will have a varying velocity of propagation of light, according to the sound waves. This varying velocity of propagation of light, will result in a varying phase shift of the light beam, and this can be detected using interferometric means, which are well known.

DETAILED DESCRIPTION OF THE INVENTION

Figure 1:
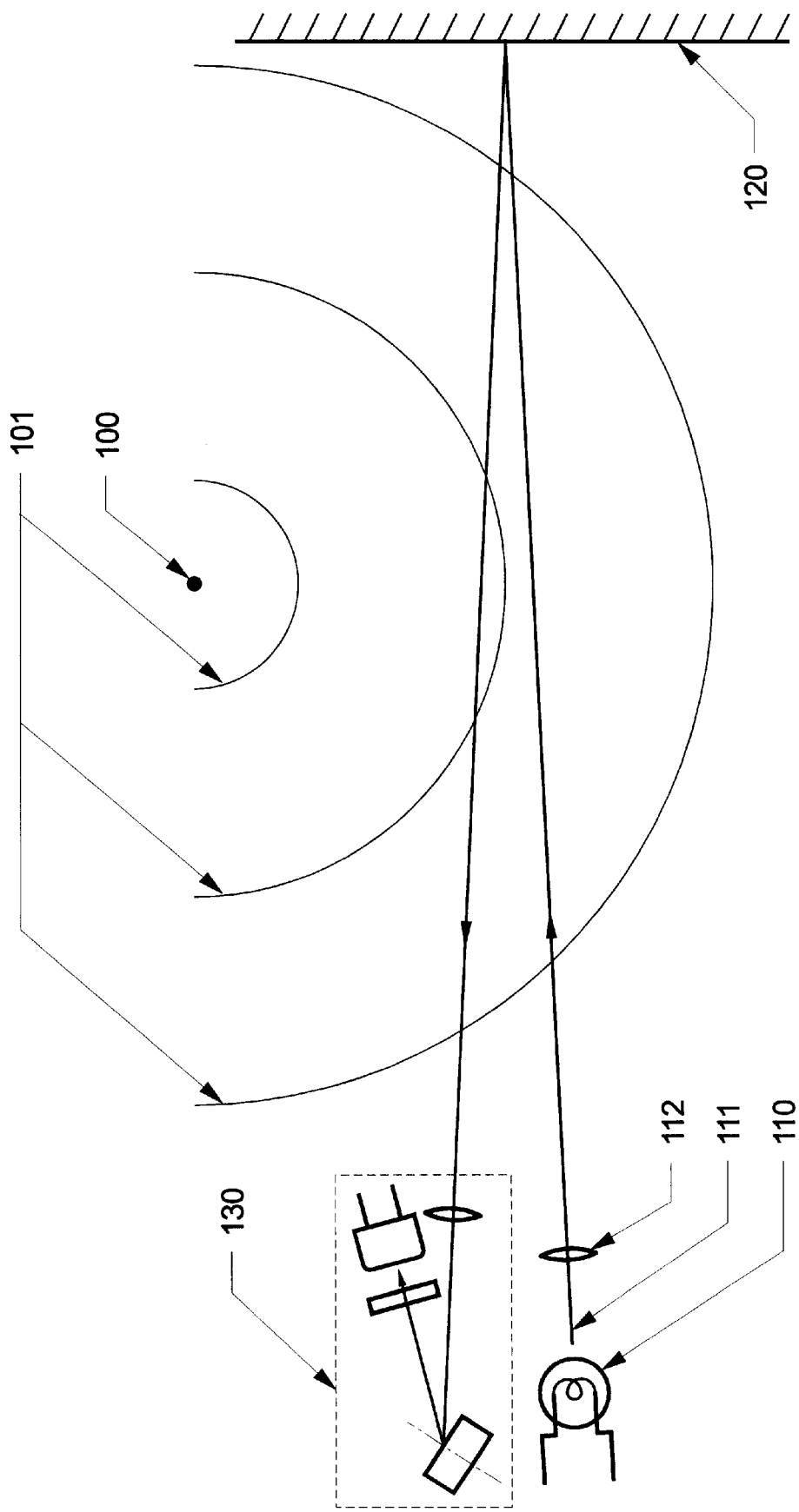
FIG. 1 shows a plan view of a possible embodiment of an attenuation method described by the present invention. The light path is substantially transverse to the propagation of the sound waves.

FIG. 1 shows a plan view of the main components of a possible embodiment of the invention. A sound source 100 emanates sound waves 101 (and others, not shown) in air, such sound waves being shown where they would be at one instant in time. While sound waves typically propagate somewhat spherically from the sound source 100, FIG. 1 shows just the portion of sound waves which propagate forwards (such as in the direction a person is projecting their voice), and only where they intersect a horizontal plane through the sound source 100; so the sound waves in FIG. 1 are represented by hemispherical lines which delineate the peaks of the propagating sound pressure waves. The light beam 111 from light source 110 is collimated by lens assembly 112, and then passes substantially transversely through the sound waves to a surface 120. The light source 110, driven by a power supply not shown in the figure, is an incandescent lamp, such as a halogen lamp, or other source that emits a spectrum of light which includes the band or bands of wavelengths absorbed by the constituents of air whose changing density is to be monitored. Lens assembly 112 is comprised of one or more optical elements as required to ensure that the light of those wavelengths does not diverge too much to be detected by the optical receiver 130. Surface 120 could be any surface, such as a light-colored wall or floor, or a reflective surface such as a mirror or a retroreflective plastic sheeting such as 3M's "Scotchlite". Some amount of the light beam 111 then reflects back to the optical receiver 130, which is shown in more detail in FIG. 2.

As shown in FIG. 1 the light beam 111 passes through the sound waves 101 twice, increasing the effect of the sound waves 101 changing the attenuation of the light beam 111 (so long as the light beam is not significantly attenuated when it is longitudinal to the sound waves, since this attenuation reduces the sound wave's effect on the light beam's changing intensity), and this can have the beneficial result of decreasing the sensitivity requirements of the optical receiver 130. Furthermore, by using mirror assemblies (not shown in the figure, but a well known technique), multiple reflections could be utilized so that the light path 111 passes through the sound waves more than two times, and this could further increase the sound wave 101's effects of changing the attenuation of the light beam 111, and such configurations are considered part of the present invention.

Figure 7:
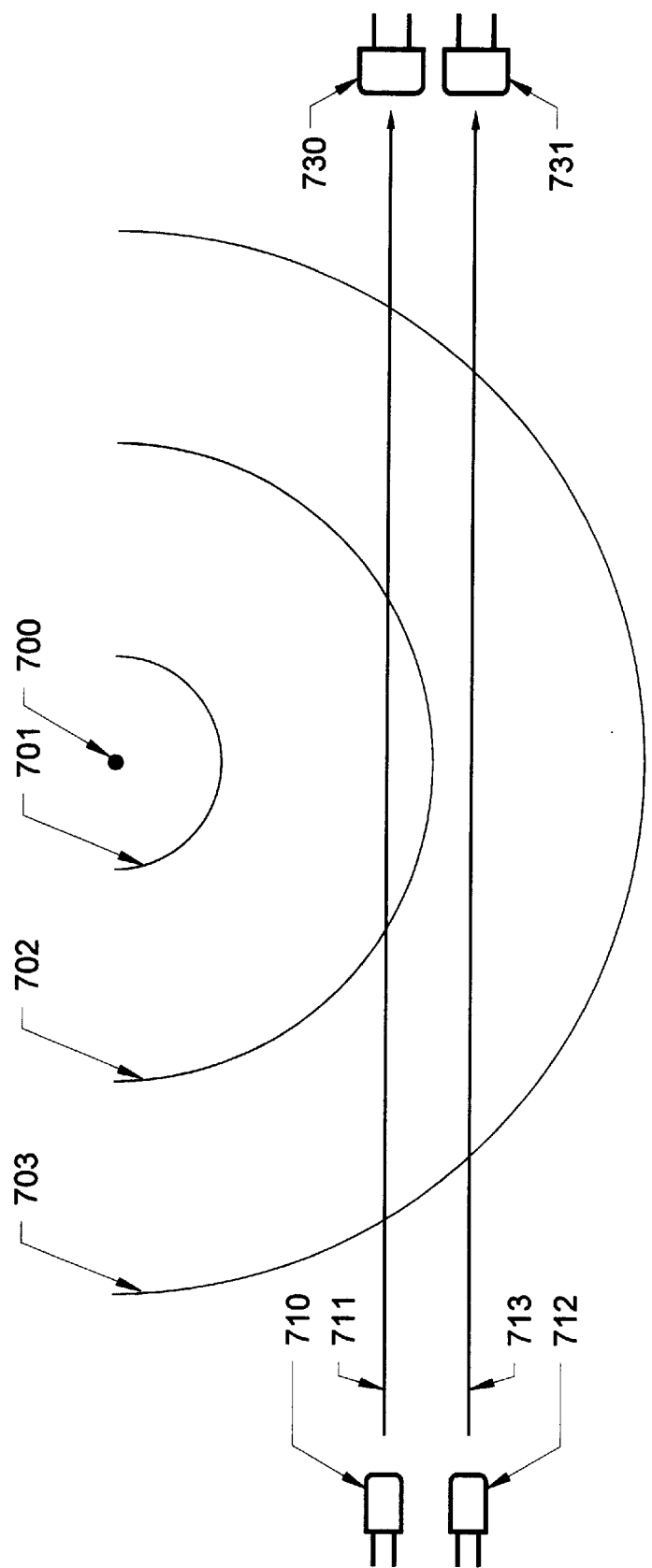
FIG. 7 shows a fourth possible embodiment of the optical receiver for this invention, where first and second photodetectors are used to enable the optical receiver to be more sensitive to sounds waves propagating in a desired direction, and less sensitive to other sound waves.

Alternatively, by locating the light source 110 and the optical receiver 130 on opposite sides of the sound source 100, the light beam 111 would only pass through the sound waves 101 once. Such an embodiment would be useful for some applications, such as shown in FIG. 7, and is also considered part of this invention.

Also, while the light beam 111 in FIG. 1 is shown to be horizontal, it could also be vertical 120 could be the floor in front of the sound source 100. This would be useful in situations such as where there are multiple sound sources, or where obstructions to the sides of the sound source could block the path of a horizontal light beam.

Figure 2:
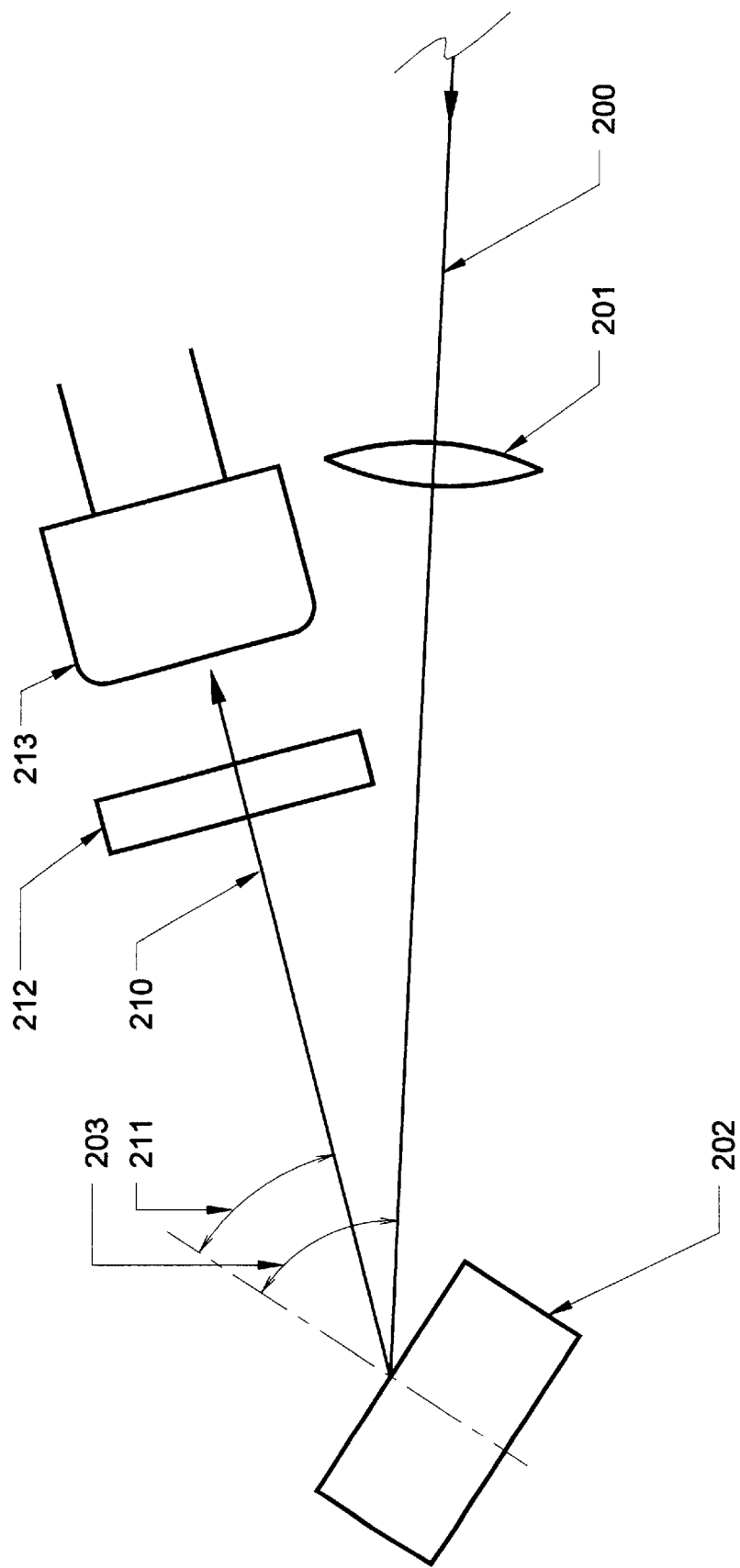
FIG. 2 shows an enlargement of the main components of the optical receiver shown in FIG. 1. A diffraction grating is used to select the particular wavelength of light to be monitored.

FIG. 2 shows a detailed view of the optical receiver 130 shown in the dashed line box in FIG. 1. The received light beam 200 (which is the reflection of light beam 111 in FIG. 1) is focussed by lens assembly 201 onto diffraction grating 202, which could be an Edmund Scientific D43,748, which has 600 grooves per millimeter. The diffracted light beam 210 then passes through filter 212 to photodetector 213. Filter 212 could be a Schott RG1000 longpass filter, which has a 50% transmittance cut-off at 1,000 nm. Filter 212 ensures that higher order diffracted modes of shorter wavelength light from diffraction grating 202 do not reach photodetector 213. A filter with a longer cut-off wavelength may be required, depending on the wavelengths emitted by the light source. Photodetector 213 could be an Optoelectronics Textron model OE-25-51 lead sulphide photodetector, which has a peak spectral response at 2.2 $\mu$m and a time constant of 200 82 s to 400 $\mu$s (providing an audio frequency response of up about 2,500 Hz to 5,000 Hz), both of which are adequate for this application. However, a model with lower detector noise and possibly greater detectivity may be required.

An electronic circuit, not shown in the figure, then processes the signal from the photodetector 213 to drive a loudspeaker or other device as required. The design and specifications required of this optical receiver and electronic circuit are well known by those familiar with the field of optical spectroscopy, with the addition that this circuit may require a higher frequency response, depending on the audio frequency response requirements of the application. For example, telephone quality audio frequency response is up to about 3,000 Hz, but typical public address sound systems have a higher maximum frequency than this.

The angle of incidence 203 of the incoming light beam 200, and the angle of the diffracted light beam 211 select the wavelength of light presented to photodetector 213. The equations relating these angles and wavelengths of light are well known to those familiar with diffraction gratings. For example, as shown in FIG. 2, if angle 203 is 60° and angle 211 is 48.4°, then the wavelength of light beam 210 will be 2.69 $\mu$m.

Note that by using a suitable lens assembly 201, ambient light, instead of a light source 110 from FIG. 1 could also be used to drive the optical receiver.

One of the decisions in the design of a particular embodiment of the present invention is the selection of the wavelength of light to monitor for changing attenuation due to the sound waves. As shown in the table below, since nitrogen and oxygen are the constituents of typical atmospheric air with the highest concentrations, their characteristic absorption bands could be good choices for the optical receiver to monitor.

| Constituent of Air | Concentration (%, by volume) | |
| --- | --- | --- |
|  | Typical Air | Exhaled Air |
| Nitrogen ($N_2$) | 77.1 | 76.7 |
| Oxygen ($O_2$) | 20.7 | 16.7 |
| Carbon dioxide ($CO_2$) | .03 | 4.0 |
| Water vapor ($H_2O$) | 1.2 | 2.6 |

Another choice would be to monitor the light attenuation at an absorption wavelength for carbon dioxide or water vapor, since these constituents of air are exhaled by people (and animals) in much greater concentration than is generally in the atmosphere, as shown above (these numbers vary according to many factors, such as the relative humidity and altitude, but are representative). Happily, some of the absorption wavelengths for carbon dioxide and for water vapor are very close to each other (for example, 2.69 $\mu$m for carbon dioxide and 2.66 $\mu$m for water vapor), reinforcing the changing attenuation effect, thereby making this band of wavelengths a good choice to monitor. In this case, the light path should pass closely past the mouth of the sound source, since the exhaled carbon dioxide and water vapor quickly dissipates into ambient air. Such a choice of wavelength to monitor would permit the sound waves produced by people and animals to be detected at a much greater distance, since the changing (due to the sound waves) light attenuation effect would then be much greater in the immediate vicinity of the sound source, thereby reducing the changing attenuation effect caused by other unwanted ambient sounds. This is shown in greater detail in FIG. 5.

In this embodiment, sound source 300 has produced sound waves 301, 302, and 303, and light source 310, driven by a power supply not shown, emits a beam of narrow spectrum light 311 which passes through sound waves 303 and 302. monitored for attenuations discussed above. As is shown in FIG. 3, the optical elements required to collimate the light may be built-in to the light source 310, so may not need to be separately part of the light path.

Figure 3:
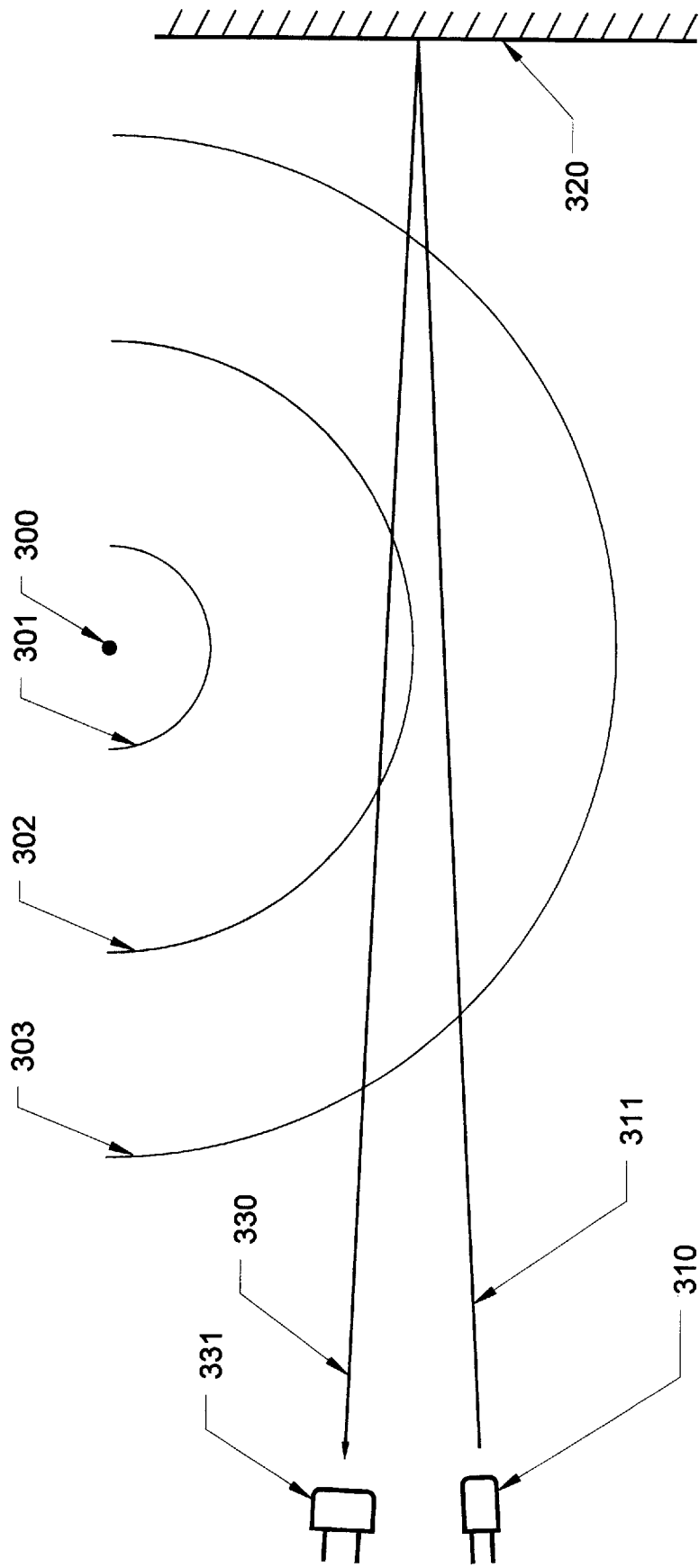
FIG. 3 shows a second possible embodiment of the optical transmitter and receiver for this invention. Specifically, a narrow band light source and a simpler optical receiver are used.

Similarly, depending on the design of the light source 310 and any required transmitting optics, the photodetector 331 may not require a lens assembly, as is shown in FIG. 3. Furthermore, depending on the design and orientation of the photodetector 331 and the ambient lighting conditions, simplified filtering (such as only a longpass interference filter), or no filtering at all may be required for the received light 330 being detected by the photodetector 331.

As above, an electronic circuit, not shown in the figure, would be needed to process the signals produced by photodetector 331, in order to produce an electrical signal suitable for driving a speaker or other equipment. Finally, the selection and specifications of the light source 310, photodetector 331, and the design of the electronic circuit and any optical filtering and other optics required are well known to those familiar with optical spectroscopy.

As described below, the changing attenuation or changing velocity of propagation of light effect due to sound waves is greatest for light paths which are substantially transverse to the direction of propagation of the sound waves. Accordingly, FIGS. 4A and 4B show two possible configurations which can be used when it is required to locate the light source and optical receiver substantially in front of the sound source.

Figure 4:
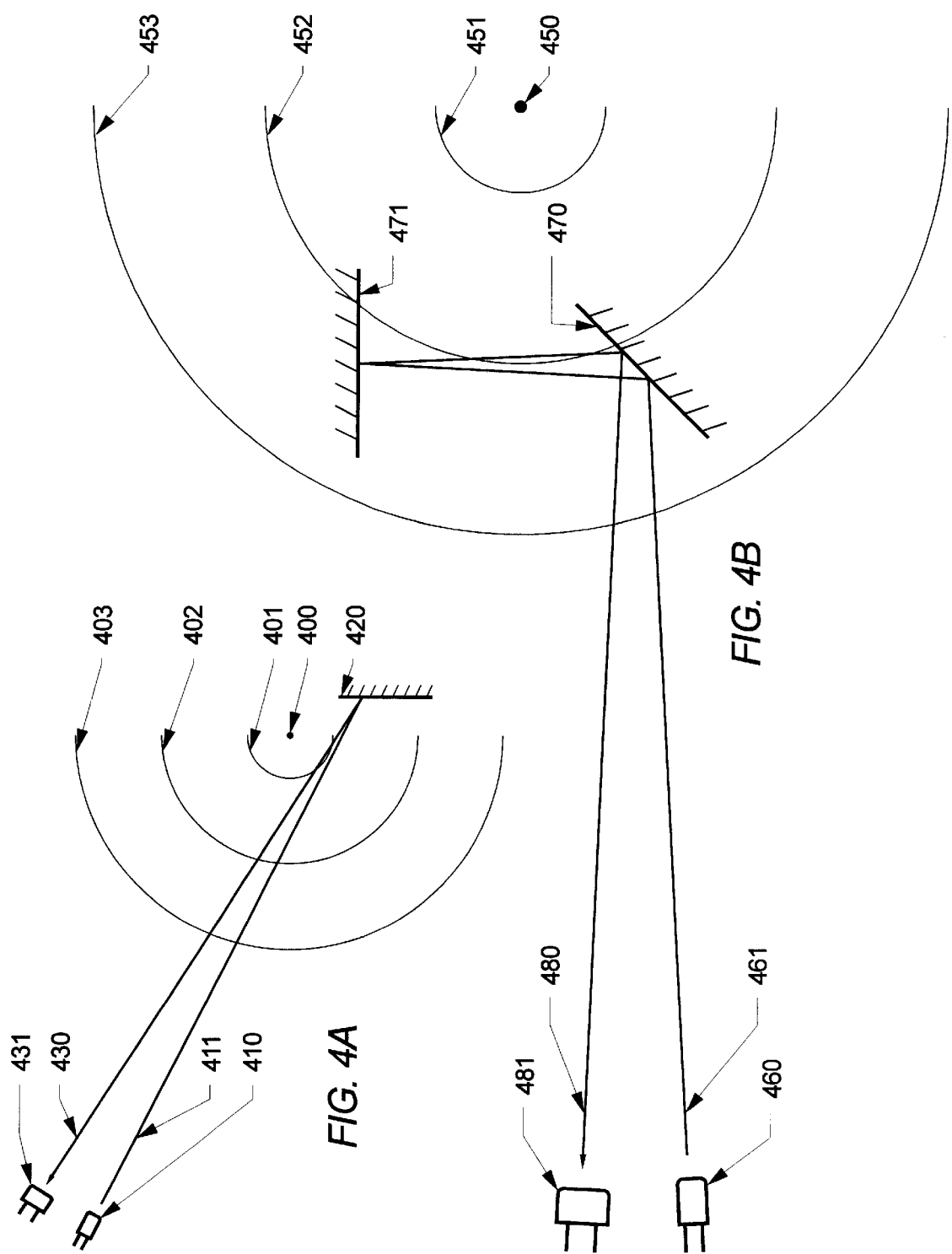
FIG. 4 shows a second and third possible embodiment of the light path to be used, so that the light path is still transverse to the sound waves even when, for example, the optical receiver needs to be somewhat in front of the sound source.

FIG. 4A shows sound source 400 has produced sound waves 401, 402, and 403. By directing light source 410 to the side of sound source 400, the light path 411 will still be tangential to sound waves closer to the sound source 400, in this case, specifically to sound wave 401. A retroreflecting surface 420 is shown, however, other reflecting surfaces as described above could be used. The returning light path 430 impinges on photodetector 431, though other optical receiver configurations could be used, as described above.

FIG. 4B shows first and second reflecting surfaces 470 and 471, for changing the direction of the light so that part of the light path is transverse to the direction of propagation of the sound waves 451, 452 and 453 emanated by sound source 450. Light source 460 is directed so that light path 461 impinges on first reflecting surface 470, which could be a mirror, which is angled so that the reflected light is substantially transverse to the sound waves, in the figure this is to sound wave 452. Second reflecting surface 471 could be a retroreflecting surface, or a mirror which is positioned so that it directs reflected light back to first reflecting surface 470, which then directs the reflected light beam 480 to optical receiver 481.

Note that other configurations are possible, such as using a single reflecting surface 470 to direct the returning light 480 to optical receiver 481, however the source of the light could be either ambient light or the light source 460 could be located in place of second reflecting surface 471.

Finally, note that while these figures have emphasized configurations where the light beam is transverse to the direction of propagation of the sound waves to be detected, a light beam longitudinal to the propagation of the sound waves would still result in a varying received light intensity according to the sound waves. However, this effect would be due to the actual bulk motion of the air molecules due to the sound waves, and this would have a much smaller effect on the optical characteristics of the medium than the other configurations described herein. The present invention includes such other configurations.

Figure 5:
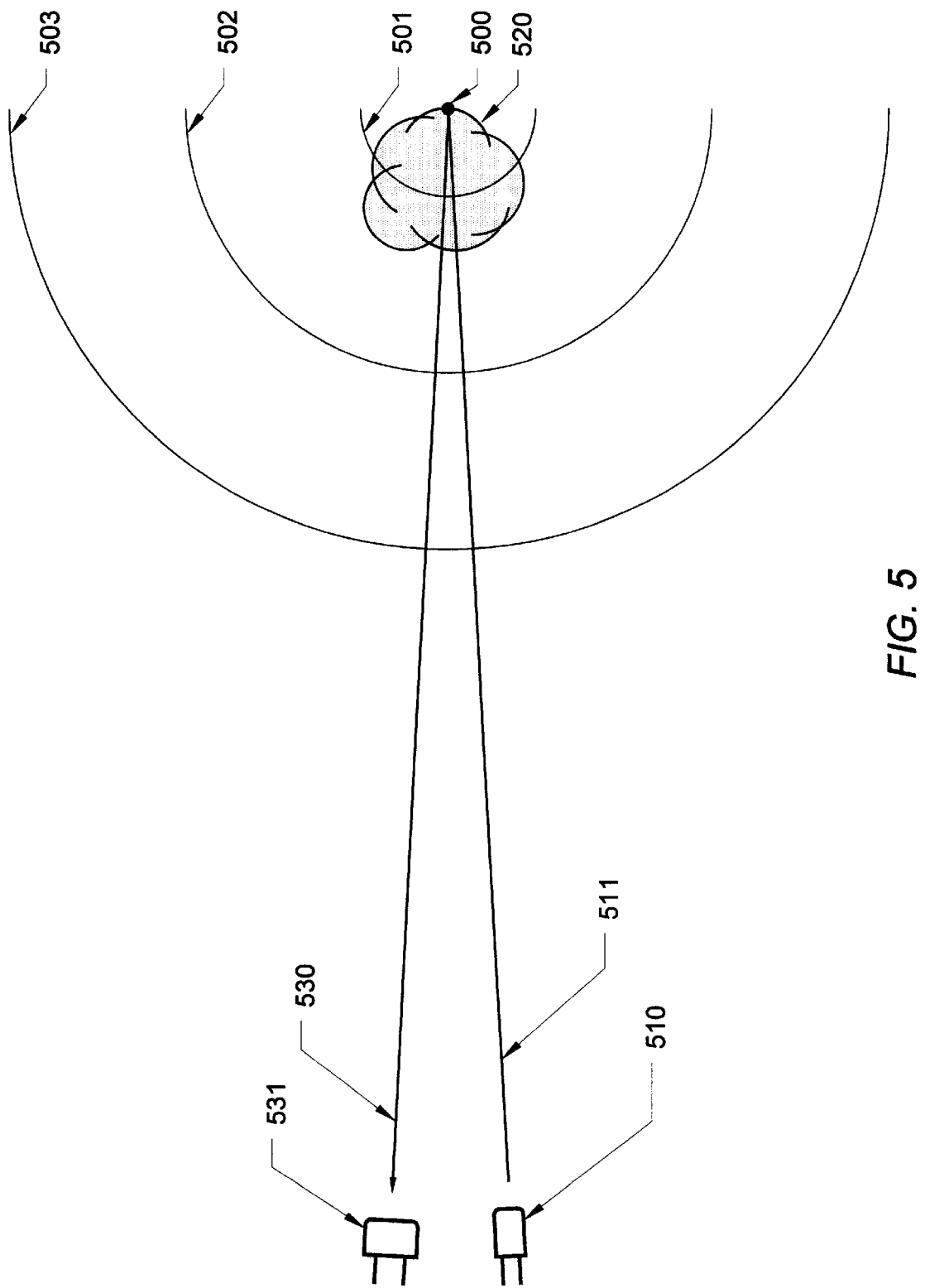
FIG. 5 shows a fourth possible embodiment of the light path which can be used for this invention. The light path can be used in some situations when the wavelengths of light are those which are highly absorbed by constituents of air which are exhaled by the sound source.

FIG. 5 shows an alternate method of detecting sound waves, again using attenuation of specific wavelengths of light. However, in this configuration the light beam does not need to be transverse to the direction of propagation of the sound waves. As shown in the table above, people and animals exhale carbon dioxide and water vapor in much higher concentrations than are generally in the atmosphere. This "cloud" of carbon dioxide and water vapor near, and downwind from, a speaking person's mouth dissipates into the atmosphere, at a rate depending primarily on any air currents and the temperature. If the size of the cloud is less than about ½ the wavelength of the sound to be detected (or a small number of wavelengths more), then there will still be a net change in the attenuation of light passing through the cloud, even when the light path is longitudinal to the direction of propagation of the sound waves, as shown in FIG. 5, and further in FIG. 11. This occurs since the attenuation of the light beam 511 is significantly greater in the cloud than in the path between the light source and the cloud, so the net attenuation change for light path 511 is, for example, proportional to the average of a sine wave from a phase angle of 0° to 180°, which is non-zero.

Specifically, light source 510 emits light 511 which includes wavelengths which are highly absorbed by carbon dioxide or water vapor, such as wavelengths from 2.66 $\mu$m to 2.76 $\mu$m, and is directed towards the sound source 500. Light beam 511 passes through the cloud of carbon dioxide or water vapor 520 near the mouth of the sound source, which has emitted sound waves 501, 502 and 503. A portion 530 of light beam 511 reflects back to the optical receiver 531 due to the light beam 511 impinging on the sound source 500's face, glasses or other surface of or worn by the sound source 500, or due to a reflective surface, such as a light colored wall, retroreflector, mirror or other surface near, on, or past the sound source 500.

Return light beam 530 is then received by optical receiver 531. As above, a lens assembly or other optic elements, not shown in the figure, may be required to be part of the optical receiver, and such are well known.

Other configurations are possible, such as; locating the optical receiver 531 on the opposite side of the sound source 500 from the light source 510, or using a diffraction grating or other filtering means to select a narrow band of wavelengths from a broad spectrum light source, and other variations described herein.

Figure 6:
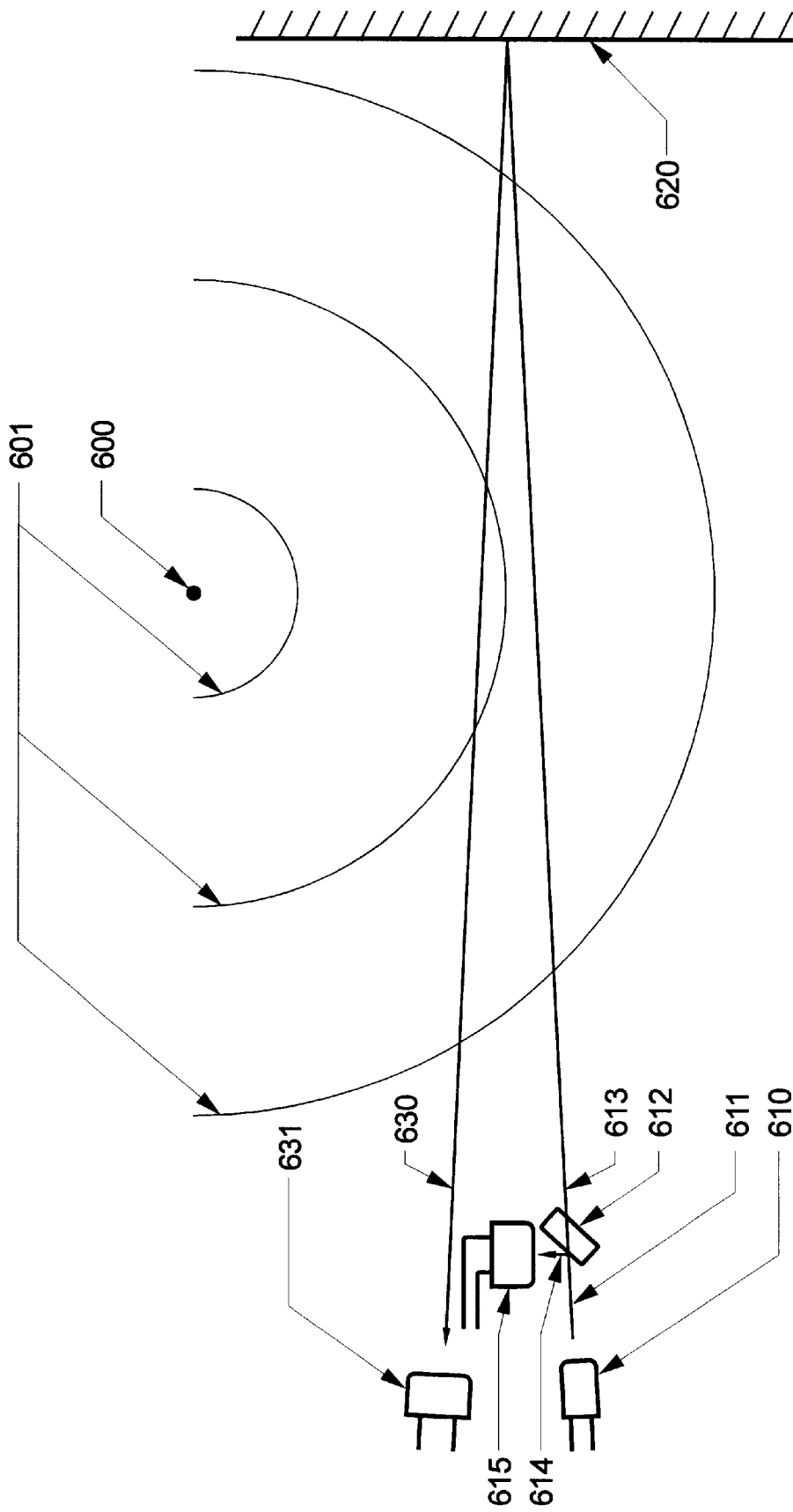
FIG. 6 shows a third possible embodiment of the optical receiver for this invention, where a first photodetector receives the light after passing through the sound waves and a second photodetector is utilized to continuously monitor the output power of the light source so that the optical receiver can reduce the noise otherwise caused by light source output variations.

The intensity variations of the returned light beam due to the changing attenuation as a result of the sound waves can be very small, in the order of 1 PPM (part per million) or less, depending on the amplitude of the sound waves and other factors. To detect this signal, eliminating noise, such as intensity variations of the light beam due to causes other than the sound waves of interest, is a major design goal of the light source and optical receiver. Such requirements are common in instrumentation design, and a range of techniques are well known, such as modulating the light source and using synchronous detection, cooling the photodetector to increase its detectivity, using multiple photodetectors to reduce detector noise, and monitoring the light source power output to detect spurious output variations. An example of the latter technique is shown in FIG. 6. A portion 614 of the light output 611 from light source 610 is directed to second photodetector 615, using a partially silvered mirror 612 or other means, such as a prism-based beam splitter. Light source 610 is driven by a power supply, not shown in the figure. Other configurations of monitoring the output of light source 610 are possible, and are well known.

The portion 613 of light source 610's output 611 that is not reflected by partially silvered mirror 612 then passes through the sound waves 601 emanated by sound source 600, and is reflected by surface 620 back through the sound waves 601 as light beam 630. The intensity variations of received light beam 630 due to the changing attenuation of the constituent or constituents of the air due to the sound waves 601 are then monitored by photodetector 631. As described earlier, using filtering, a diffraction grating, a light source that emits a narrow band of wavelengths of light or other means, the photodetector 631 monitors the intensity variations for specific wavelengths of light which are highly absorbed by specific constituents of air.

The signals from first and second photodetectors 631 and 615 are processed by an electronic circuit, not shown in the figure. The electronic circuit can then cancel out variations in the intensity of received light beam 630 which are in fact due to spurious output changes of light source 610, rather than due to the changing attenuation of the constituent of the air due to sound waves 601.

FIG. 7 shows a configuration of the present invention which can be used to sense sounds crossing the light beams 711 and 713 substantially from a desired direction only. Again, for clarity, the light sources 710 and 712 are shown to emit just the narrow band of wavelengths desired, and the optical receivers 730 and 731 include whatever light filtering is required, but other techniques of selecting the wavelengths to monitor can equally be used, as discussed above.

Light sources 710 and 712 direct light beams 711 and 713 through the sound waves 703 and 702 which were emanated by sound source 700, and the beams 711 and 713 impinge on photodetectors 730 and 731, which then detect the changing attenuations of the light beams 711 and 713.

Other configurations are possible, for example, using a single light source and a beam splitter or diverging lens assembly, not shown in the figure, to produce the light for both photodetectors 730 and 731. This configuration would have the substantial benefit of eliminating variations in the intensity of the received light beams due to variations in the output power of one of the light sources, and such techniques are well known.

Sound waves 701, 702 and 703 propagate at the speed of sound, so the changing attenuation of light beam 711 due to the sound waves and as detected by photodetector 730 will substantially equally occur for light beam 713 and detected by photodetector 731 a fixed time later, according to the distance between the light beams 711 and 713. By suitable processing of the signals from photodetectors 730 and 731 by an electronic circuit, not shown in the figure, the sound waves which, for example, originate in the plane of light beams 711 and 713 and first pass light beam 711 at a right angle, and then pass light beam 713 can be detected, while sound waves that traverse light beams 711 and 713 in other directions can be substantially ignored due to the different time delay between their passing the light beams 711 and 713.

There are many other configurations that also provide directionality, and such are also considered part of the present invention. For example, the light source or sources could be on the same side of the sound waves as the photodetectors and a reflective surface used, similar to that shown in FIG. 3. Also, more than two photodetectors, arranged in a linear array for example, could be used to provide a feature such as additional directionality, or sensitivity to specific frequencies of sound waves, through suitable signal processing by an electronic circuit. Also, rather than a linear array of photodetectors, a 2-dimensional matrix of photodetectors could be used to provide a feature such as to selectively detect sounds which originate from a source above or below the plane of a linear array, or to identify the direction of propagation of sound waves. Such time-delay based signal processing is a well known digital signal processing technique.

Figure 8:
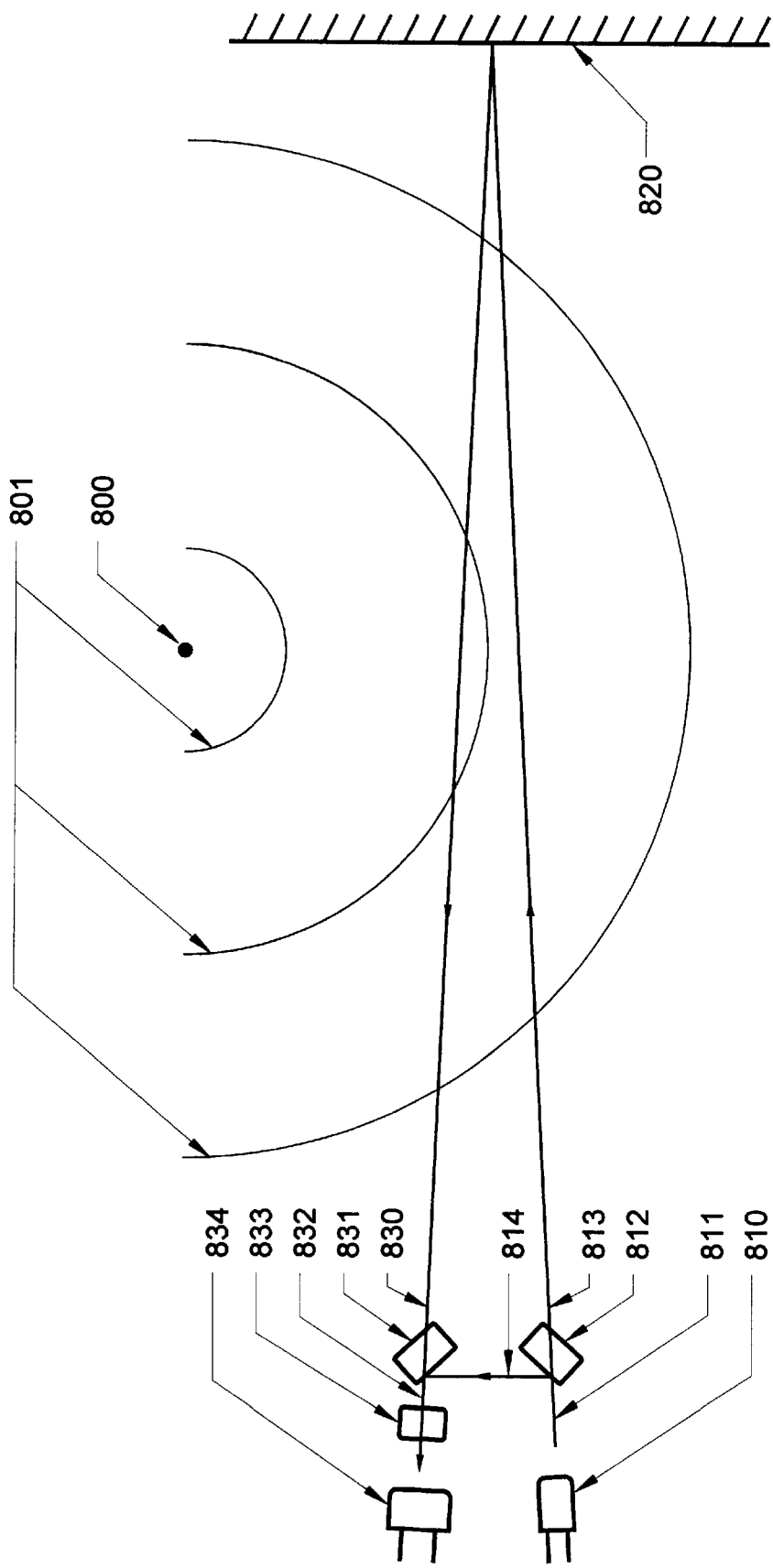
FIG. 8 shows a method of detecting sound waves based on interferometry, rather than attenuation along the light path.

FIG. 8 shows an interferometry based method of detecting sound waves. Since the density of air, for example, affects the velocity of propagation of light through it, as the air's density changes due to sound waves, the velocity of light will change accordingly, and this can be detected through phase shifts in a light beam which travels transversely through the sound waves. For maximum sensitivity, a shorter wavelength of light should be used, since smaller changes of velocity can be detected due to the corresponding greater phase shift produced for such smaller wavelengths and also because shorter wavelengths of light propagate more slowly in air, and therefore have greater velocity changes due to a given density change.

In FIG. 8, light source 810 produces coherent light 811 with a coherence length at least equal to the path length from light source 810 to reflecting surface 820 and back to photodetector 834. Light source 810 is driven by a power supply not shown in the figure. First partially silvered mirror 812 directs a portion 814 of the light to second partially silvered mirror 831. The other portion 813 of light 811 from light source 810 continues through first partially silvered mirror 812 and through sound waves 801 emanated by sound source 800, to reflecting surface 820, where it continues as light beam 830, again passes through sound waves 801, and passes through second partially silvered mirror 831 and combines with the reflected portion of light beam 814 as light beam 832. Depending on the relative phase of the two light beams 814 and 830, and the alignment of the first and second partially silvered mirrors 812 and 831, the intensity of light beam 832 will change, or the interference fringes produced will shift, according to the sound waves 801, and this will be detected by photodetector 834. A combination of Ronchi grating, lens assembly 833, matrix of elements in photodetector 834, or other techniques according to the type of interferometer used would be employed to detect the phase shift. An electronic circuit, not shown in the figure would be used to process the signal from photodetector 834, and drive a speaker or other device.

There are many configurations of interferometers that could be used in place of that shown in FIG. 8, and others may have benefits such as allowing a light source with a shorter coherence length to be used, or being more sensitive to small phase shifts. Such configurations are well known to those familiar with the field of interferometry, and are considered part of the present invention. Also, other configurations of this interferometer based method, such those described elsewhere herein; for example, the longitudinal method shown in FIG. 5 and the directional method shown in FIG. 7, are also considered part of the present invention.

Figure 9:
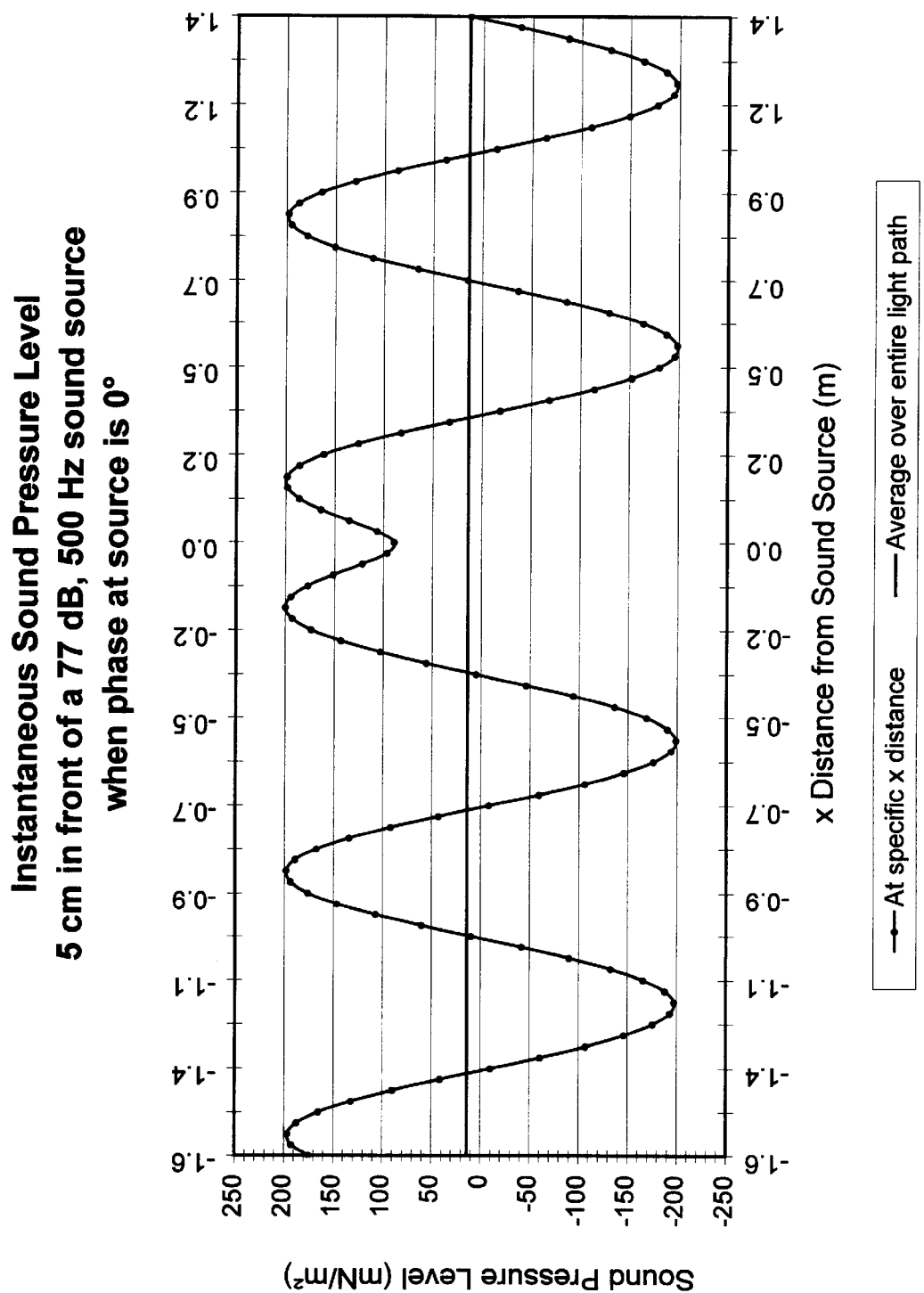
FIG. 9 shows a graph of the sound pressure level for each point along a light path such as one shown in FIG. 7, at an instant in time when the phase of sine wave emanating from the sound source is at 0°
Figure 10:
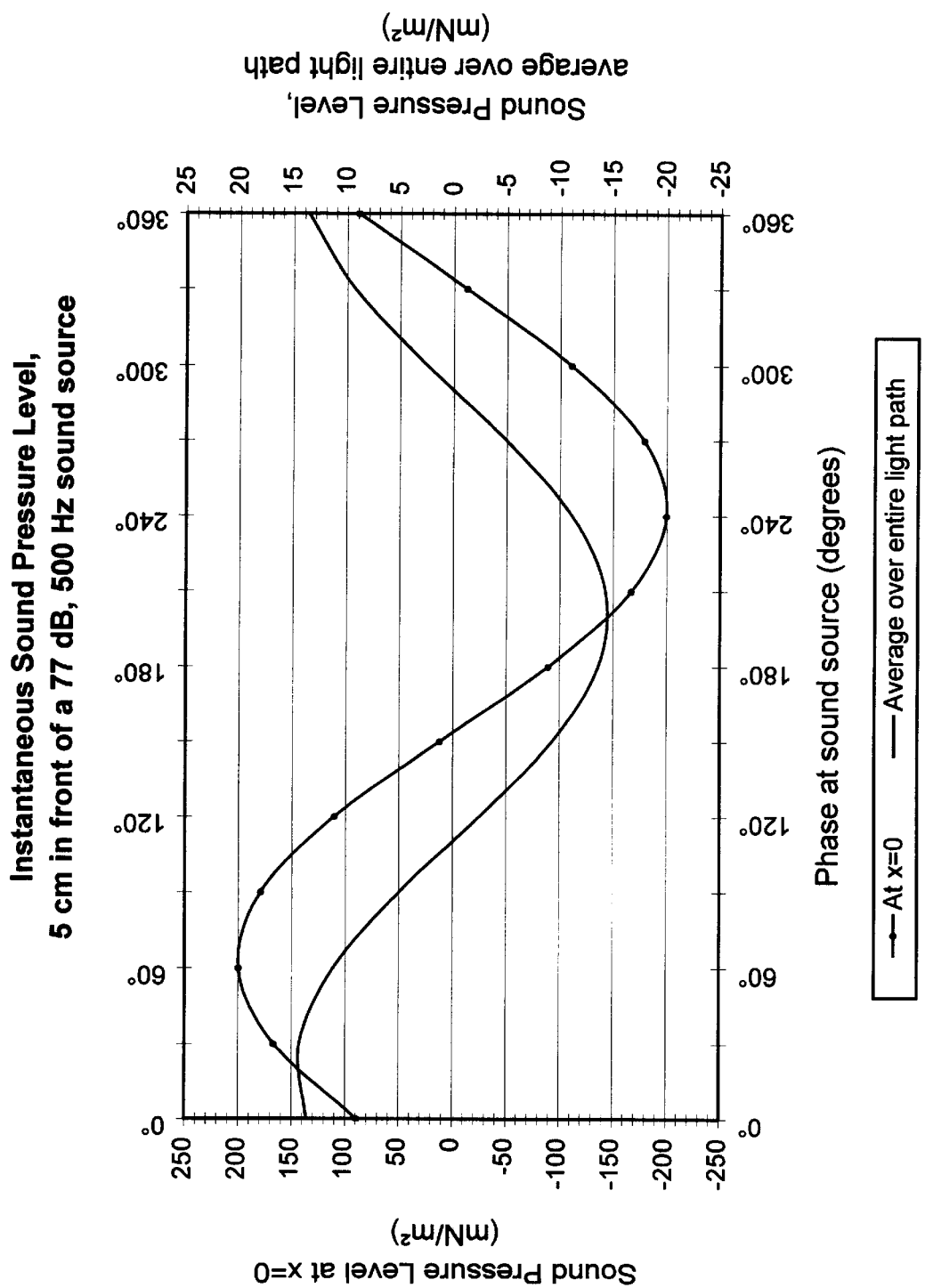
FIG. 10 shows a graph of the sound pressure level averaged along the entire light path, as the phase of the sound source advances. This changing averaged sound pressure level causes an attenuation and phase shift of the light, according to the sound waves through which it passes.
Figure 11:
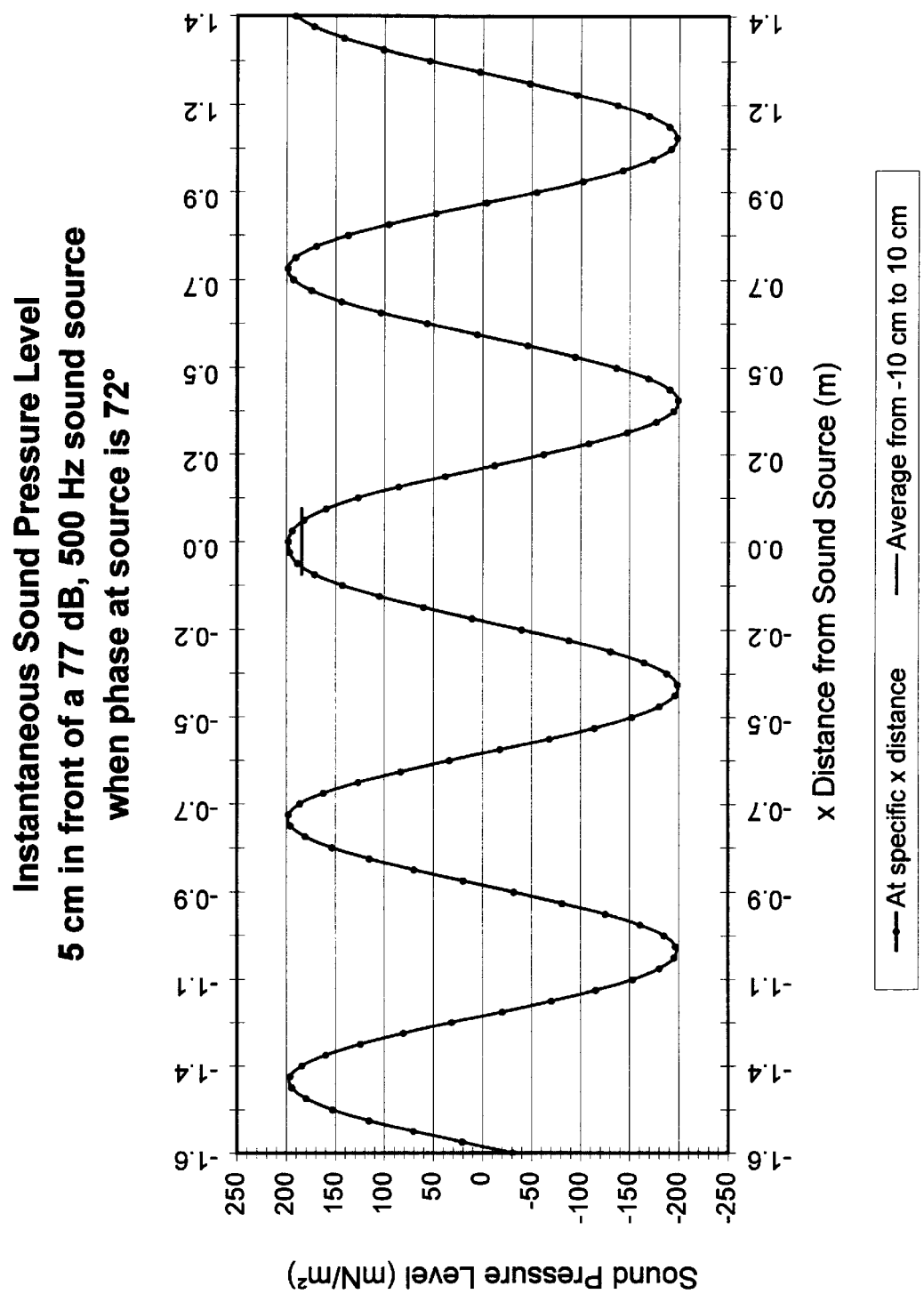
FIG. 11 shows a graph of the calculated sound pressure level, for a light path such as one shown in FIG. 5, where most of the attenuation occurs near the sound source.

FIG. 9 is a graph of the calculated instantaneous sound pressure level for each point along a light path similar to that shown for light beam 711 in FIG. 7, at the instant when the emanating sound waves 701, 702 and 703 from sound source 700 are in the relative orientations shown in FIG. 7. As is standard in the field of acoustics, sound pressure levels, such as that on the ordinate axis of the graph in FIG. 9, are measured, calculated and shown relative to atmospheric air pressure. The equations used for the calculations and graphs for FIGS. 9, 10 and 11 are routine for those familiar with acoustics and spectroscopy.

The exact shape and amplitude of the curve in FIG. 9 depends on many factors, such as the distance of the light beam 711 from the sound source 700, the attenuation of sound with distance, and the frequency, phase and amplitude of the sound waves emanated by the sound source 700, but the curve is representative. The curve in FIG. 9 was calculated for a 500 Hz sine wave, with an originating sound pressure level of 77 decibels (dB)—which is a typical loud speaking amplitude—with the light path 711 a constant y distance (that is, down the page of FIG. 7) of 5 cm from the sound source 700, and starting an x distance (that is, across the page of FIG. 7) of −1.6 meters (111) from the sound source and ending at 1.4 m past the sound source, as shown on the abscissa of the graph. As shown in FIG. 9, light beam 711 encounters greater density air, and therefore greater optical attenuation and lower velocity of propagation of light as the light beam passes through the sound wave compression peak 703 shown in FIG. 7, and this is shown in FIG. 9 by the peak in the sound pressure level of about 200 mN/M² (that is, 0.2 N/m²) at an x distance of about −0.85 m from the sound source. The light path 711 continues through a minimum compression (more correctly called rarefaction) of the air between sound waves 703 and 702, resulting in the minimum sound pressure level of about −200 mN/m² at an x distance of about −0.55 m from the sound source, shown in the graph in FIG. 9.

As shown in FIG. 9, between x distances −1.6 m and −0.5 m (for example) the light path 711 crosses the sound waves, such as 703, mostly longitudinally (as shown in FIG. 7), and the instantaneous sound pressure level changes with distance in substantially a sinusoidal fashion between these v distances, as shown in FIG. 9. The average sound pressure level taken over this entire distance of −1.6 m to −0.5 m, at this, and also at later instants in time, is therefore substantially zero, so there will be substantially no net change in the optical attenuation or velocity of light for a beam of light travelling over this path, over a period of time.

However, as the light path 711 approaches and passes the sound source 700 and the light path 711 is substantially tangential to sound wave 702 (as shown in FIG. 7)—between x distance −0.5 m and 0.5 m—the instantaneous sound pressure over this distance is no longer sinusoidal (as shown in FIG. 9), and the instantaneous average sound pressure taken over this distance will be non-zero. So for this x distance of −0.5 m to 0.5 m, over time, there will be a change in the attenuation and the velocity of light according to the frequency of the sound waves produced by sound source 700. The amplitude of this change will depend on the amplitude of the sound waves 701, 702 in 703, and also on the distance over which the light path is somewhat tangential to the sound waves—which in turn depends on both the frequency of the sound waves (lower frequencies have greater effect since the sound waves have greater distance between them) and the distance of the light path from the sound source (at greater distances, sound waves have greater radius, so the light path is tangential to the sound wave over a greater distance, and so has greater effect).

The horizontal line at about 14 mN/m² in FIG. 9 is the average of the sound pressure level at an instant of time (when the phase at the sound source is 0°), over the entire path length of −1.6 m to 1.4 m. As an approximation, this means that a light beam from x distance −1.6 m to 1.4 m at that instant in time will have an attenuation or phase shift as if it had travelled through a constant air pressure about 14 mN/m² higher than atmospheric air pressure, even though it has actually travelled through varying sound pressure levels of 200 mN/m² to −200 mN/m² that average out over time to a sound pressure level of zero.

FIG. 10 shows a curve of this instantaneous average sound pressure level encountered along a light path such as 711 in FIG. 7, over time (note that it is about 14 mN/m² at 0°, as shown by the horizontal line in FIG. 9), as the phase of the sound source advances from 0° to 360°. For reference, FIG. 10 also shows the curve of the sound pressure level at a point 5 cm directly in front of Sound source 700 (that is, at an x distance of 0 m). The graph shows that while the phase is shifted, and the amplitude decreased, the original sinusoidal sound pressure level generated by sound source 700 and detected perhaps by traditional means such as a standard microphone at a point, is reproduced as a correspondingly changing sound pressure detected along a straight path such as light path 711, and this will result in a correspondingly changing optical attenuation along the entire light path 711. Specifically, for this example, the sound pressure level measured at the point would have a peak amplitude of about 200 mN/m², and the sound pressure level measured along the light path would have a peak amplitude of about 14 mN/m².

Therefore, as shown in FIGS. 9 and 10, sound waves passing through a beam of light will result in corresponding changes to the optical attenuation along the light path. However in FIGS. 9 and 10, because the instantaneous sound pressure level along the light path was taken as the average for the entire light path, the calculation applies to the optical attenuation for a constituent of air which occurs in a substantially constant concentration along the entire light path. Also, as the distance between the sound source and the optical receiver increases, the change in optical attenuation Belong the light path decreases, thus limiting the distance over which sound waves can be detected with an acceptable signal to noise ratio.

By utilizing a wavelength of light which is attenuated mostly near the sound source, sound waves at a much greater distance from the optical receiver can be detected. As shown above, people and animals exhale carbon dioxide and water vapor, and these constituents of air will be in much higher concentration near the mouth of people speaking, for example. Therefore, attenuation changes for wavelengths of light absorbed by these particular constituents of air will not be reduced as match along the light path as for wavelengths which are absorbed by, for example, nitrogen and oxygen which are present in approximately equal concentration along the entire light path. As an example, attenuation of 2.69 $\mu$m wavelength it or a 10 cm path length of carbon dioxide gas at 4% concentration by volume in atmospheric air (that is, for exhaled air) is equal to the attenuation for approximately a 13.3 m path length of carbon dioxide at 0.03% concentration (that is, for typical atmospheric air).

FIG. 11 is similar to FIG. 9 in that the graph is of the calculated instantaneous sound pressure level for each point along a light path, such as that in FIG. 5. Also as for FIG. 9, the calculations are for a light path 5 cm in front of a 500 Hz, 77 dB sound source, however in this case the phase at the sound source is 72° —which is near the phase angle that results in the maximum optical attenuation along the light path length of interest. And that path of interest in this case is from an x distance of −10 cm to 10 cm only, as this is a possible size for the "cloud" of carbon dioxide in front of a person speaking (the cloud size changes, but slowly enough that this can be filtered out by the electronic circuit, since the cloud size changes at a rate substantially different from audio frequencies). Over the part of the light path which is outside of the cloud, the attenuation is much lower, as shown above. As shown by the short horizontal line in FIG. 11, the average sound pressure level at the instant when the sound source is at 72°, for the −10 cm to 10 cm path in the cloud, is about 185 mN/m².

Since the optical attenuation is related to both the path length and the density of the absorbing constituent of air, the greatest optical attenuation change for a path at an instant in time, will occur for a path length of slightly less than a ½-wavelength through this cloud (greater than this reduces the average, less than this reduce the path length of greater attenuation, and therefore the signal strength). Also, note that:

unlike the earlier examples which had a substantially constant air constituent density along the light path, the light path through this cloud can be at any angle (transverse, longitudinal, or a component of both) to the direction of propagation of the sound waves, and the one-way path length through the cloud (that is, the diameter of the cloud) can be greater or less than the above approximately ½-wavelength, but the optical attenuation change will be accordingly less.

For the attenuation method of detecting sound waves; the absorbance of light in a gas is proportional to the path length times the density of the absorbing medium, the transmittance is the percentage of light remaining after passing through the medium, and these are related as follows:

$$Absorbance = \log_{10}\left(\frac{1}{Transmittance}\right)$$

Therefore, further calculations can be done to quantify the effect on a beam of light for the following situations:

For the attenuation of the wavelengths of light absorbed by oxygen or nitrogen, for example, the average sound pressure along the entire path of the light beam 711 would be used to calculate the change in absorbance, and from that and the path length, the change in light transmittance would be calculated, as this would be the change in light intensity measured at photodetector 730.

For the attenuation of the wavelengths of light absorbed by carbon dioxide or water vapor, the average sound pressure for the distance that light beam 711 travels through the area of higher concentration of carbon dioxide or water in front of the sound source's mouth, and the path length through this cloud of carbon dioxide or water vapor would be used to calculate the change in absorbance, and from that the change in light transmittance would be calculated, as this would be the change in light intensity measured at photodetector 730.

For example, page 264 of the Sell-Ettre Encyclopedia of Industrial Chemical Analysis, 1969 edition, volume 8, shows that at 2.69 μm, the transmittance through a 10 cm path length of carbon dioxide at 200 torr is about 50%. From the equation above, a transmittance of 50% is equivalent to an absorbance of 0.301030. And 200 torr represents a concentration of about 26.32% by volume in atmospheric air (taking 760 torr as atmospheric pressure). Near a speaker's mouth the concentration of carbon dioxide is about 4%, so calculating the absorbance for a round trip path (assuming the return path through the carbon dioxide cloud is 20 cm), and then the transmittance from this, would be as follows:

$$Absorbance_{(at\ 50\%\ transmittance)} = \log_{10}\left(\frac{1}{0.5}\right)$$
$$= 0.301030$$

$$Absorbance_{(at\ 4\%\ concentration\ and\ 20\ cm\ path\ length)} = 0.301030 \times$$
$$\frac{4\%}{26.32\%} \times \frac{20\ cm}{10\ cm}$$
$$= 0.091513118$$

$$Transmittance = 10^{-0.091513118}$$
$$= 81.000347\%$$

As shown in FIG. 11, the sound pressure level over the path length in the cloud, due to the 77 dB, 500 Hz tone is about 0.185 N/m², and this should be reduced by the attenuation along the rest of the path, which is about 4% (for a 5.8 m path at 0.03% concentration, which is a factor of 0.96). Atmospheric air pressure is about 101,325 N/m², so the transmittance in the presence of a peak in the sound pressure level in the cloud is calculated as follows:

$$Absorbance_{(at\ 185\ mN/m^2\ sound\ pressure\ level)} = 0.091513118 \times$$
$$\frac{(0.96 \times 0.185)\ N/m^2\ +}{101,325\ N/m^2}$$
$$\frac{101,325\ N/m^2}{}$$
$$= 0.091513279$$

$$Transmittance = 10^{-0.091513279}$$
$$= 81.000317\%$$

Therefore, the change in transmittance due to the presence of sound waves is from 81.000347% to 81.000317%, which is a change of about 0.3 PPM.

For the interferometry method of detecting sound waves, the average sound pressure along the entire path of the light beam 711 and the entire path length of the light would be used to calculate the phase shift for the wavelength of light emitted by light source 710. This would then show the interference fringe shift expected at photodetector 834 in FIG. 8, for example.

Such calculations are routine to those familiar with the fields of spectroscopy and interferometry.

Therefore, what I claim as my invention is:

1. An optical method for remotely sensing vocal sounds produced by a selected person, comprising:
  a) utilizing one or more sources of light, each of which produces a broad spectrum of wavelengths of light including wavelengths which are highly attenuated by carbon dioxide gas,
  said selected person exhaling as part of producing vocal sound, and said exhaling producing a cloud of air with a higher concentration of carbon dioxide gas than is found generally in atmospheric air,
  c) providing one or more light detectors, each of which is paired with a corresponding one of said one or more sources of light,
  d) said one or more light detectors, over said broad spectrum of wavelengths of light, is sensitive only to light received in a predetermined narrow range of wavelengths of light, said predetermined narrow range of wavelengths of light being among those which are highly attenuated by carbon dioxide gas,
  e) directing said one or more sources of light along a path through said cloud of air to said corresponding one of said one or more light detectors,
  f) said one or more light detectors each producing an output signal which varies according to the intensity of said light received in said predetermined narrow range of wavelengths, whereby sound waves in said cloud of air and crossing a said path have a greater effect on said intensity of said light received by said corresponding one of said one or more light detectors than do sound waves outside of said cloud of air, and
  whereby vocal sound waves can be remotely and selectively sensed according to said light received.

2. The method of claim 1, wherein said one or more sources of light is ambient light.

3. The method of claim 1 wherein more than one said source of light and light detector pair is utilized and wherein said paths intersect said cloud of air and said output signals from said more than one light detectors are processed by adding them together, whereby sound waves in said cloud of air and passing said paths have a greater effect on said processed output signals than do sound waves outside of said cloud of air, and whereby remote vocal sound waves can be sensed.

4. An optical method for remotely sensing vocal sound waves produced by a selected person, comprising:

a) providing more than one source of light, each of which produces a predetermined narrow range of wavelengths of light, b) said selected person exhaling as part of producing vocal sound waves, and said exhaling producing a cloud of air with a higher concentration of certain constituents than is generally found in atmospheric air, c) said predetermined narrow range of wavelengths of light being among those which are highly attenuated by said certain constituents, d) providing more than one light detector, each of which is paired with a corresponding one of said one or more sources of light, e) directing each said source of light along a path through said cloud of air to each said source of light's corresponding said light detector, f) each of said one or more light detectors detecting the intensity of light received from its corresponding said source of light, and producing an output signal which varies according to the intensity of said light received, g) processing said output signals from said light detectors by adding them together, whereby sound waves in said cloud of air have a greater effect on said processed output signals than do sound waves outside of said cloud of air, and whereby remote vocal sound waves can be sensed.

5. The method of claim 1 or 4, wherein more than one said source of light and light detector pair is utilized, a) at least two of said light detectors being predetermining arranged so that a sound wave from said selected person first affects said intensity of light received at a first light detector, and at an expected time-delay time later affects said intensity of light received at a second light detector, b) processing said output signals by delaying said output signal from said first light detector by said expected time-delay and then adding this to said output signal from said second light detector, whereby said processed output signals due to said vocal sounds produced by said selected person are reinforced, while said output signals due to undesired sources of sounds which arrive from other directions are reduced, whereby said output signals provide improved selectivity and directionality.

6. The method of claim 1 or 4, wherein more than one said source of light and light detector pair is utilized, and a) the minimum distance from said selected person to each of said paths through said cloud of air is equal, and b) processing said output signals from said light detectors by adding them together, whereby said processed output signals due to said vocal sounds produced by said selected person are reinforced, while said output signals due to undesired sources of sounds which arrive from other directions are reduced, whereby said output signals provide improved selectivity and directionality.

* * * * *